US009626481B2

(12) United States Patent
Solomon et al.

(10) Patent No.: US 9,626,481 B2
(45) Date of Patent: Apr. 18, 2017

(54) DOSE COUNTER AND RECORDING METHOD

(71) Applicant: TEVA PHARMACEUTICAL INDUSTRIES LTD., Petach Tikva (IL)

(72) Inventors: Ian Solomon, Jerusalem (IL); Moti Goldhirsh, Kfar Saba (IL)

(73) Assignee: Teva Pharmaceutical Industries Ltd., Petach Tikva (IL)

(*) Notice: Subject to any disclaimer, the term of this patent is extended or adjusted under 35 U.S.C. 154(b) by 394 days.

(21) Appl. No.: 13/925,113

(22) Filed: Jun. 24, 2013

(65) Prior Publication Data

US 2014/0032243 A1    Jan. 30, 2014

Related U.S. Application Data

(63) Continuation of application No. 12/855,685, filed on Aug. 12, 2010, now Pat. No. 8,539,945.

(60) Provisional application No. 61/234,657, filed on Aug. 18, 2009.

(51) Int. Cl.
G06F 19/00 (2011.01)
A61M 15/00 (2006.01)

(52) U.S. Cl.
CPC ....... G06F 19/3431 (2013.01); A61M 15/008 (2014.02); A61M 15/009 (2013.01); A61M 15/0065 (2013.01); A61M 2205/332 (2013.01); A61M 2205/502 (2013.01)

(58) Field of Classification Search
CPC .......... A61M 15/009; A61M 2205/332; A61M 2205/502; A61M 15/0065; A61M 15/008; A61M 15/00; A61M 2205/3306; A61M 2205/3317; A61M 2205/3553; A61M 2205/3592; A61M 2205/6027; A61M 2205/6054; A61M 2205/6063; A61M 2209/01; G06F 19/3431
USPC ............ 128/200.11, 200.12, 200.13, 200.14, 128/200.15, 200.16, 200.17, 200.18, 128/200.19, 200.21, 200.22, 200.23, 128/200.24, 203.12, 203.15, 205.23; 705/3
See application file for complete search history.

(56) References Cited

U.S. PATENT DOCUMENTS

| 5,363,842 | A | 11/1994 | Mishelevich et al. |
| 5,411,173 | A | 5/1995 | Weinstein |
| 5,482,030 | A | 1/1996 | Klein |
| 5,505,192 | A | 4/1996 | Samiotes et al. |
| 5,544,647 | A | 8/1996 | Jewett et al. |
| 5,622,163 | A | 4/1997 | Jewett et al. |

(Continued)

Primary Examiner — Lynne Anderson
Assistant Examiner — Elliot S Ruddie
(74) Attorney, Agent, or Firm — Condo Roccia Koptiw LLP

(57) ABSTRACT

A dose counter for a metered dose inhaler includes a force sensor, an electronic controller, a memory for storing data indicative of a remaining number of doses and an electronic display device coupled to the controller for displaying the remaining number of doses. The dose counter is attached or integrated into a base of a canister containing medicament such that force applied to the base of the canister is registered by the force sensor, the controller being configured to measure force applied to the dose counter when depressing the canister and being responsive to measured force to decrement the remaining number of doses stored in the memory and shown on the display device.

21 Claims, 5 Drawing Sheets

(56) References Cited

U.S. PATENT DOCUMENTS

| | | |
|---|---|---|
| 5,676,129 A | 10/1997 | Rocci, Jr. et al. |
| 5,809,997 A | 9/1998 | Wolf |
| 6,029,659 A | 2/2000 | O'Connor |
| 6,138,669 A | 10/2000 | Rocci, Jr. et al. |
| 6,148,815 A * | 11/2000 | Wolf ........................ 128/205.23 |
| 6,283,365 B1 | 9/2001 | Bason |
| 6,405,727 B1 | 6/2002 | MacMichael et al. |
| 6,431,168 B1 | 8/2002 | Rand et al. |
| 6,446,627 B1 | 9/2002 | Bowman et al. |
| 6,659,307 B1 | 12/2003 | Stradella |
| 6,761,161 B2 | 7/2004 | Scarrott et al. |
| 7,331,340 B2 | 2/2008 | Barney |
| 7,587,988 B2 | 9/2009 | Bowman et al. |
| 7,637,227 B2 | 12/2009 | Stradella et al. |
| 2004/0255936 A1 | 12/2004 | Urbanus |
| 2006/0254581 A1 | 11/2006 | Genova et al. |
| 2007/0295329 A1 | 12/2007 | Lieberman et al. |
| 2008/0017193 A1 | 1/2008 | Jones et al. |
| 2008/0066742 A1 | 3/2008 | Hodson et al. |
| 2009/0139516 A1 | 6/2009 | Augustyn et al. |
| 2009/0194104 A1 | 8/2009 | Van Sickle |
| 2009/0229607 A1 * | 9/2009 | Brunnberg .......... A61M 15/008 128/203.15 |
| 2011/0031038 A1 | 2/2011 | Page |

\* cited by examiner

DOSE COUNTER AND RECORDING METHOD

CROSS-REFERENCE TO RELATED APPLICATIONS

This application is a continuation of U.S. patent application Ser. No. 12/855,685, filed Aug. 12, 2010, which claims priority to U.S. Provisional Patent Application No. 61/234,657, filed Aug. 18, 2009, both of which are incorporated herein by reference in their entirety for all purposes.

FIELD OF THE INVENTION

The present invention is in the field of dose counters for metered dose inhalers (MDIs). There is a regulatory requirement to either display the number of doses remaining within the device or show whether the spray canister is exhausted, and the present invention provides an electronic dose counter which supplies such an indication in a simple manner.

BACKGROUND OF THE INVENTION

The idea of having a dose counter is well known in the art, and a number of potential implementations for such a counter exist. U.S. Pat. No. 5,363,842 describes an inhaler which detects how much air is inhaled through it and during what course of time, including such measurements as the triggering of the release of aerosol, and also incorporates a dose counter.

U.S. Pat. No. 5,411,173 describes a counter device attachment for a depressible spray dispenser for products such as medicine. The dispenser comprises a clip to fit about the side wall of the dispenser's casing, a foot-leg positioned beneath the dispenser and connected to the clip, and a counter actuated by the shaft which moves within a shaft housing, wherein a button on the counter is incremented each time the tank is depressed.

U.S. Pat. No. 5,482,030 describes a counter for a spray container implementing a counting disk showing the number of activations. U.S. Pat. No. 5,544,647 and U.S. Pat. No. 5,622,163 describe an electronic counting device mounted on the exterior of the housing, which indicates the number of doses remaining in the canister as signaled by a switch activated by the canister movement.

U.S. Pat. No. 5,505,192 describes an electronic dispenser monitoring circuit mounted on the canister, comprising an elastomeric membrane switch which serves to count the number of doses given. U.S. Pat. No. 5,676,129 describes a dose counter based on the use of a miniature pressure sensor which detects the pressure pulse in the transfer channel of the mouthpiece of the MDI through which the inhaler dose is released. U.S. Pat. No. 5,809,997 describes a dose counter attached to the inhaler housing incorporating a strain gauge sensing extending through a hole in a side of the housing for engaging a portion of the canister next to the valve stem. The sensing arm senses when the valve stem of the canister is properly compressed for release of medication.

U.S. Pat. No. 6,029,659 describes an inhaler inside a housing of which a dose counter is activated by a push button that is depressed when force is applied to the canister. U.S. Pat. No. 6,138,669 describes the use of a miniature pressure sensor and microprocessor to detect the pressure pulse in the transfer channel of the mouthpiece of the MDI through which the inhaler dose is released. U.S. Pat. No. 6,283,365 describes a dose counter attached or attachable to the base of the canister, comprising a spring-loaded cap which is depressed in relation to a second part mounted on the domed base of the canister. Within the cap is a pair of independently rotatable rings, where each depression of the cap relative to the canister, causes the first ring to rotate and thus implement a mechanical counter. U.S. Pat. No. 6,405,727 describes a dose counting mechanism based on a wheel with a toothed disc portion and a smooth disc, the smooth disc of the wheel bearing digits 00 to 20 and the wheel bearing digits 0 to 9. When the wheels are viewed the display can show any number from 000 to 209.

U.S. Pat. No. 6,431,168 describes a mechanical, cog-based, dose indicator located within the base of the inhaler housing, by the outlet of the canister. U.S. Pat. No. 6,446,627 describes a dose indicator based on a rotary gear which moves in step-wise fashion in response to displacement of an actuator, where the rotary gear comprises a wheel having a plurality of ratchet teeth. U.S. Pat. No. 6,659,307 describes a dose counter comprising at least one flexible rotary counting element applied against and turning on a curved support surface.

U.S. Pat. No. 6,761,161 describes a dose counter comprising a ratchet wheel, a drive member selectively engaging the indicating member, a pawl selectively engaging the ratchet wheel, and a non-return member adapted to selectively engage the ratchet wheel so as to maintain a unidirectional rotation of the ratchet wheel. In one embodiment, the indicating device also includes a usage indicator member having usage indicia that indicates the number of usage cycles completed or remaining for the indicating device.

U.S. Pat. No. 7,331,340 describes an inhaler for use with a removable pressurized aerosol canister, having a display for indicating to a user the state of the canister. A memory device on the canister (or a housing which houses the canister) stores information indicative of doses dispensed from, or remaining in, the canister, where that information is processed to provide and display information representative of the state of the canister. US 20040255936 describes a disposable dose counter. US 20060254581 describes a counter module affixed to a MDI canister, and is thus differentiated from an embodiment in which the counter is affixed or built into an actuator body. The visual display is read from above the inhaler, or from a direction that is generally radial with respect to the major axis of the inhaler. Relative motion of the canister within the actuator body activates a switch component of the EDC module by means of a trigger mechanism positioned within a cap that is fixedly mounted to the canister.

US 20070295329 also describes an electronic counter module mounted on the base of the canister, where depression of the top of this module closes two contacts separated by a spring. The spring ensures that sufficient force is developed before the counter is incremented. US 20080017193 describes a dose counter comprising a sensor for directly detecting a metered medicament dose dispensed from said container through its outlet, and a visual display unit for displaying the number of metered doses of medicament used or remaining within the container.

U.S. Pat. No. 7,587,988 describes a mechanical dose indicator comprising a counter housing, a rocker arm with a pawl, the rocker arm being pivotally supported by the housing and arranged to perform a rocker movement in response to a linear actuation motion, a return spring for resetting the rocker arm, a ratchet wheel engageable with the pawl to convert the movement of the rocker arm into an incremental rotational motion of an axle arrangement, thus advancing a display means.

US 20080066742 describes a mechanical counting mechanism where the display arrangement is of pointer-gauge type with a static display section provided as an integrated part of a transparent display containing part of a counter housing. U.S. Pat. No. 7,637,227 describes a inhaler device counter for displaying remaining doses of medicine having a pointer gauge type display, integrally formed with the counter housing. US 2009139516 describes a dose counter for an inhaler having a count wheel with fixed index tooth arranged for intermittent meshing with kick teeth, such that rotation of a kick wheel results from rotation of the count wheel when intermittent meshing occurs.

Thus the prior art is broadly divided into (a) mechanical solutions with some kind of dial which is advanced mechanically after each depression of the canister, and (b) electronic devices showing the number of doses remaining on an LCD or such like. The electronic type of dose counter is further divided into those which sense the aerosol dose being released (for example using a pressure sensor located adjacent to the aerosol outlet), and those based on a switch which is actuated upon the physical depression of the canister. In the latter type, the travel or physical movement between the open and the closed position of the switch takes place either between the canister and its housing (i.e. the inhaler) or between two parts of a module attached to the canister. In either case, it is the physical travel associated with the physical depression of the canister which closes the switch and thus increments the dose counter. As with any dose counter that is not actually verifying the release of the dose but is merely based on the travel detected, there is a possibility of false positives or false negatives.

SUMMARY OF THE INVENTION

An objective of the present invention is to provide an electronic dose counter which is not based on travel and is therefore less subject to potential mechanical errors than some prior art embodiments. Further objects of the present invention include reduction of potential false positives (where the counter is decremented but the dose is not delivered) and false negatives (where the dose is delivered but the counter is not decremented).

A further objective of the invention is to provide a method for using an electronic dose counter for recording, downloading and analyzing the dosing history from one or more MDIs. Such a method may be used to enable a medical practitioner to evaluate the compliance of the patient with a medication regimen.

A still further object of the invention is to provide a method of treatment whereby the prescribing information of the relevant MDI drug recommends that the medication regimen should not be changed without the medical practitioner first evaluating the patient's compliance history.

These objectives are realized in accordance with an aspect of the invention by a dose indicator comprising a force or pressure sensor and an electronic controller; said dose indicator being attached to the base of canister of a metered dose inhaler (MDI) in order to detect the activation action of said MDI. As the patient applies pressure to the canister in order to press the canister into the inhaler device, the sensor detects that pressure has been applied to the base of the canister. Data are collected by an electronic controller that processes the input from this sensor and includes the pressure gradients and duration. Given that the canister has a known firing pattern in terms of pressure gradient and duration, the controller can implement an algorithm that can be set to decrement the dose counter only when the pressure profile detected closely matches the profile required to "fire" the canister in order to deliver the dose. Advantageously, this ensures that the potential for false positives and false negatives registered by the dose counter of the present invention is minimized. Advantageously, the approach of the present invention also obviates the need to provide some kind of mechanical travel arrangement within or associated with the dose counter, thereby reducing the potential for mechanical failure. In some embodiments, the dose counter is a miniature module, which is attached to the base of the canister and which contains all the elements required to implement the functionality of the dose counter—i.e. the pressure sensor, the controller, digital display and battery—in a thin, low-profile, module or sticker.

Furthermore, the addition of an electronic dose counter (whether such as that provided above or otherwise implemented) enables the implementation of a method of recording and downloading the history of the doses taken, and associating this history with a specific day and time. The invention provides a method of performing such recording and associated communications mechanisms for associating the dosing history with a specific date and time.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
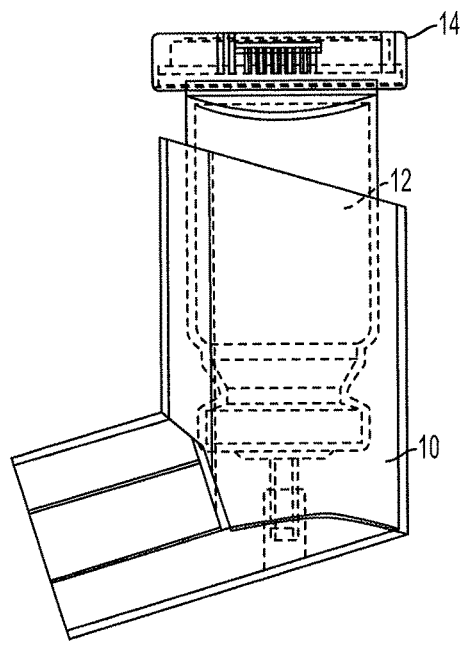
FIG. 1A provides a cut-away cross-sectional view showing the location of the dose counter on the canister and inhaler arrangement.

The operating principle of the dose counter is that it is able to capture data from its force sensor component in order to determine with a high degree of accuracy whether a dose has been administered from an MDI. Referring now to FIG. 1A, the overall configuration of a typical MDI is shown, showing a housing 10, a canister 12 and a dose counter 14 mounted on, adhered to or otherwise affixed to the base of the canister 12. When a patient presses the base of the canister 12 in order to administer a dose of aerosol from the MDI, the pressure applied to the base of the canister 12 can be measured and thereby serve an input to the dose counter.

Figure 1B:
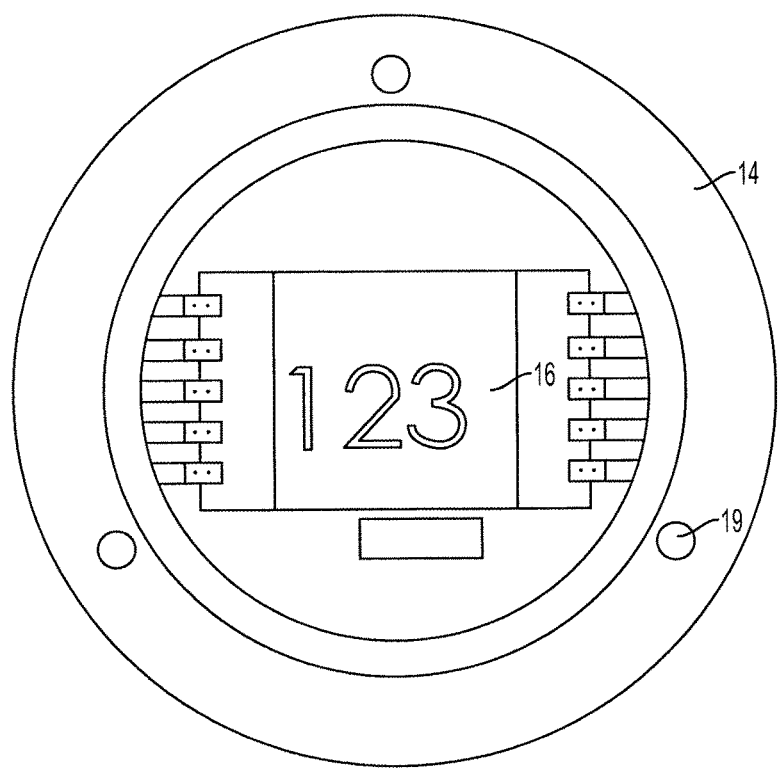
FIG. 1B shows a planar view of a preferred embodiment of the dose counter.

Referring now to FIG. 1B, an embodiment of the dose counter 14 is shown, illustrating surface features including a liquid crystal display (LCD) 16 capable of displaying the number of doses remaining and one or more informative icons. The LCD preferably displays at least three digits, as many available MDIs in excess of 100 doses. The display may be configured to display the number of remaining doses (say 123 as shown), which is decremented each time the appropriate depression is performed by the patient. In the event that the first few depressions serve to prime the MDI, then the display may contain an alphanumeric display such as "PRM" until these first few depressions have been given. The optional inclusion into the LCD 16 of further icons (not shown) can serve to provide a non-numeric indication of the state of the inhaler, for example flashing when the inhaler is within the last few doses of being empty.

Further functions that the dose counter 14 can incorporate include:

An indication that the next dose is due to be taken. In this case a further icon can flash to indicate readiness. For example, if the dose is taken twice a day, then this icon can be activated 10 hours after each dose and thus, when the patient looks at the device, he knows whether he is supposed to take the next dose. This is particularly useful if the patient takes the dose and then forgets that he has done so. When he sees that this icon is not flashing, he will know that he already took the dose.

A connector 19 enabling an external device such a PC to be connected to the canister, enabling the external device to download the history of doses given (and their time intervals) for viewing by the medical practitioner. This provides the medical practitioner with a way to examine how well the patient has been compliant with the prescribed regimen.

An audible and or audio-visual alarm when a scheduled dose has been missed.

Figure 2A:
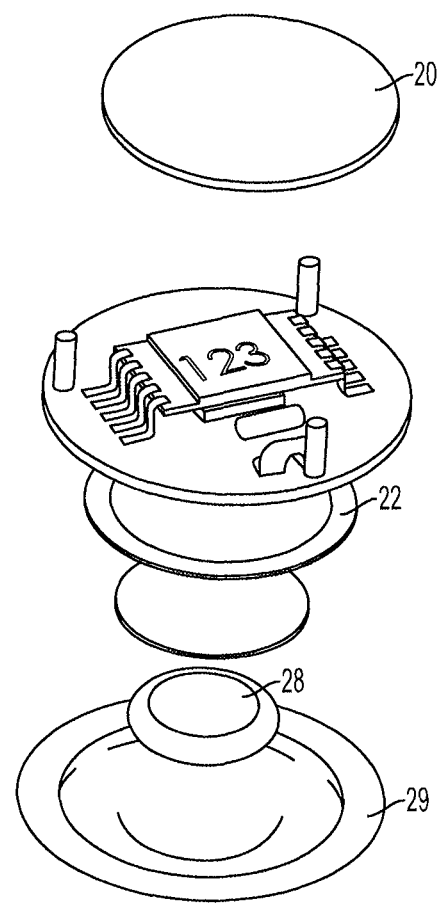
FIG. 2A shows an exploded diagram of a preferred embodiment of the dose counter, implemented as a multi-layer "sandwich"
Figure 2B:
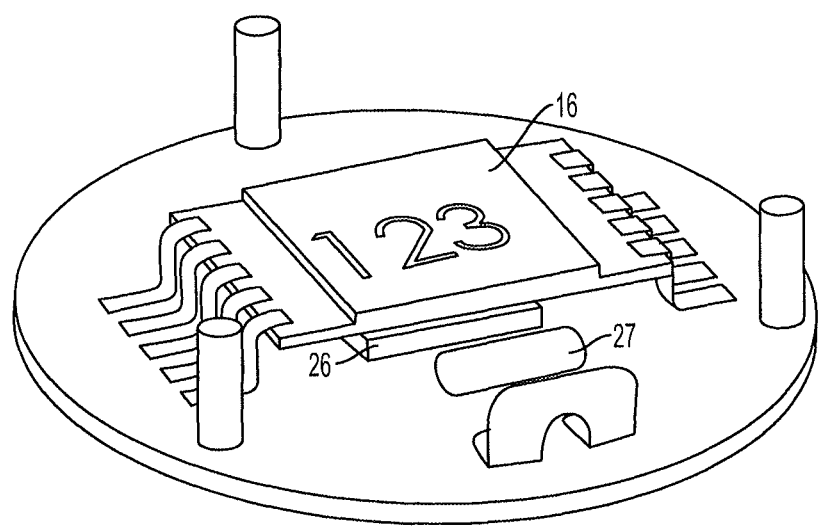
FIG. 2B shows a perspective view of the dose counter.

In some embodiments of the dose counter of the present invention, the counter is fabricated as a multi-layer "sandwich" type assemblage in order to simplify construction and minimize component costs. Referring now to FIGS. 2A and 2B, a possible layout for this assembly is provided, showing an at least partially transparent top layer 20, covering a circuit board comprising the LCD 16, a microcontroller 26, and a quartz oscillator 27 for stabilizing the time recording. The controller 26 is further connected to a force or pressure sensor such as a force sensitive resistor (FSR) 22, preferably printed or mounted on a separate layer of the sandwich as shown. An FSR is typically made of a proprietary polymer thick film ink screen printed on various substrates such that as force is applied to the device, the electrical resistance decreases. Such FSRs are available from Sensitronics LLC of 16120 Park Place, Bow, Wash. 98232, USA. Lastly, a base cover 29 serves to connect the dose counter to the canister, whether by adhesion, snap fit or any other mechanical attachment mechanism known in the art. The power for the dose controller is provided by a miniature battery 28 which may be located at least partially within a depression in the base cover 29, such that the space in the depression on the bottom of a canister can be exploited.

The layers of the dose counter may be arranged (and any internal spaces filled in) such that the dose counter constitutes a largely solid integral object which conveys the force applied on its top surface (which is the transparent layer 20 in the preferred embodiment shown) to the force sensor 22. A number of potential force or pressure sensor technologies may be used in the present invention, including but not limited to pressure sensitive resistors (FSRs), piezoelectric sensors, strain gauges, and MEMS-based sensing technologies for measuring strain and capacitance. Preferably, the force sensitive resistor extends over most of the surface area of the appropriate layer within the dose indicator, as shown in this figure.

Figure 3A:
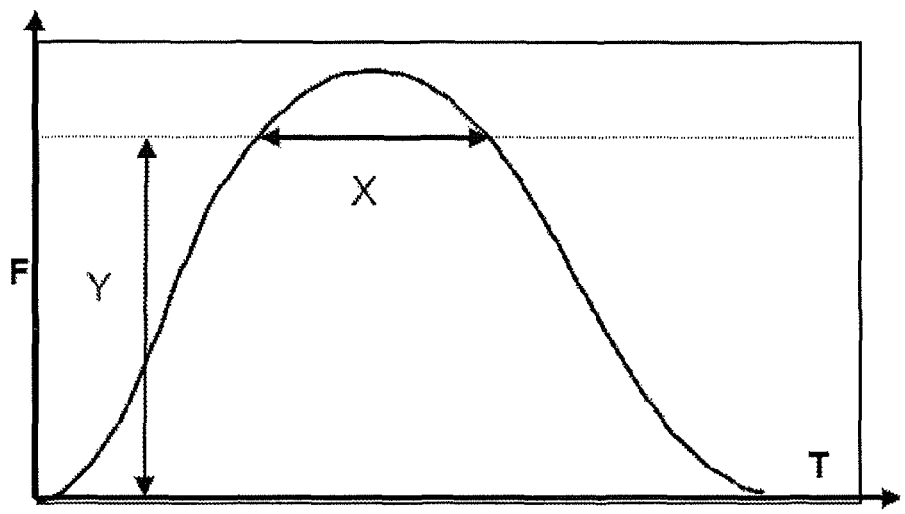
FIGS. 3A and 3B show relationships between the force/duration pattern detected by the force sensor and the firing of the dose.

Advantageously, the use of an electronic module (as opposed to a mechanical counter) enables the measurement not just of the action performed but also of the duration of this action. Thus, whereas a mechanical mechanism can show displacement, it is typically unable to show whether the displacement were maintained for sufficient time to ensure delivery of the dose. However, an electronic dose counter such as that of the present invention is capable of monitoring not only the action performed but also its duration. Referring now to FIG. 3A, a typical force vs. time curve is shown, illustrating the gradual increase in force as the base of the canister is depressed. This force reaches its peak as the canister reaches the limit of its travel and issues the dose. By setting the parameters of the electronic controller of the dose counter of the present invention such that, in a preferred embodiment, the dose counter decrements the counter only when the force exceeds a defined threshold (shown as Y) for a defined minimum duration (shown as X), the dose counter exhibits a very low level of false positives and negatives.

In order to achieve an accurate determination of when an actuation has taken place it is important to understand that the interpretation of the force applied requires a software component, and thus an electronic controller, for a number of reasons. For example, the activation force of the canister typically decreases over the number of actuations owing to aging, such that the force required for the initial actuations is significantly altered during the use of the product. For example, typical figures for "force to fire" are around 18N-20N at the start of use, gradually declining, roughly linearly, to around 15-17N as the MDI approaches the last dose (after say 120 doses). Thus, in this example, the threshold set in the software of the dose counter can for instance start at just above 18N, and then decline linearly to starting just above 15N; in order to minimize the number of false positives. The dose counter of the present invention includes a software component capable of implementing such an algorithm, which of course cannot be done using a fixed spring to determine the force applied as is done by some hitherto-proposed solutions. Furthermore, the controller of the present invention also measures the duration of the depression, so that the dose counter cannot be triggered by the device for example falling to the ground and receiving a knock on the base of the canister.

Figure 3B:
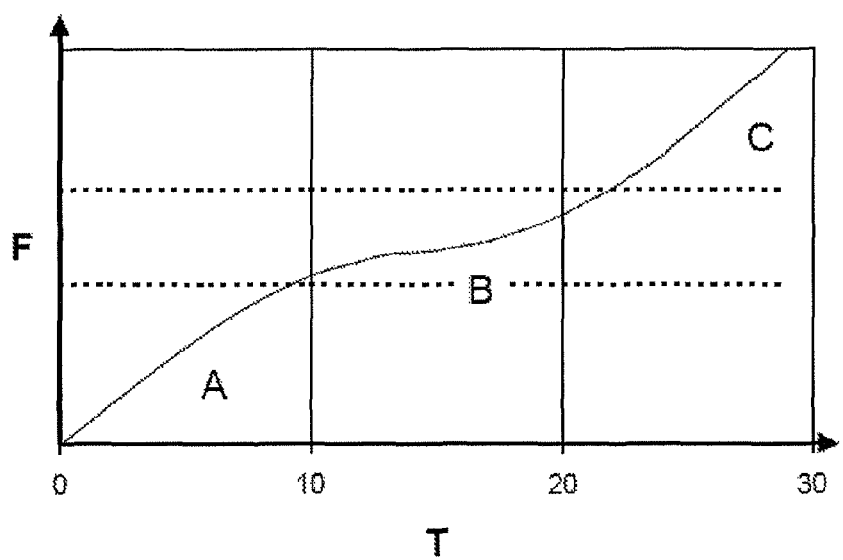

As shown in FIG. 3B, a further level of resolution may be achieved by analyzing the pattern of the increase in force in order to establish that the dose has been given. It is seen in FIG. 3B that there are three distinct zones: (A) The reaction of the canister valve spring preload force, where the slope represents the elasticity of the finger muscles; (B) The reaction force related to the valve's spring constant plus an additional drag force induced by gas flow around the valve plunger; and (C) The reaction force as the valve reaches its stop position where again the slope is related to the finger muscles elasticity. In both these embodiments, the monitoring of the force buildup (and release) over time enables a simpler method of accurately determining whether a dose has been given than alternative mechanical approaches.

Figure 4:
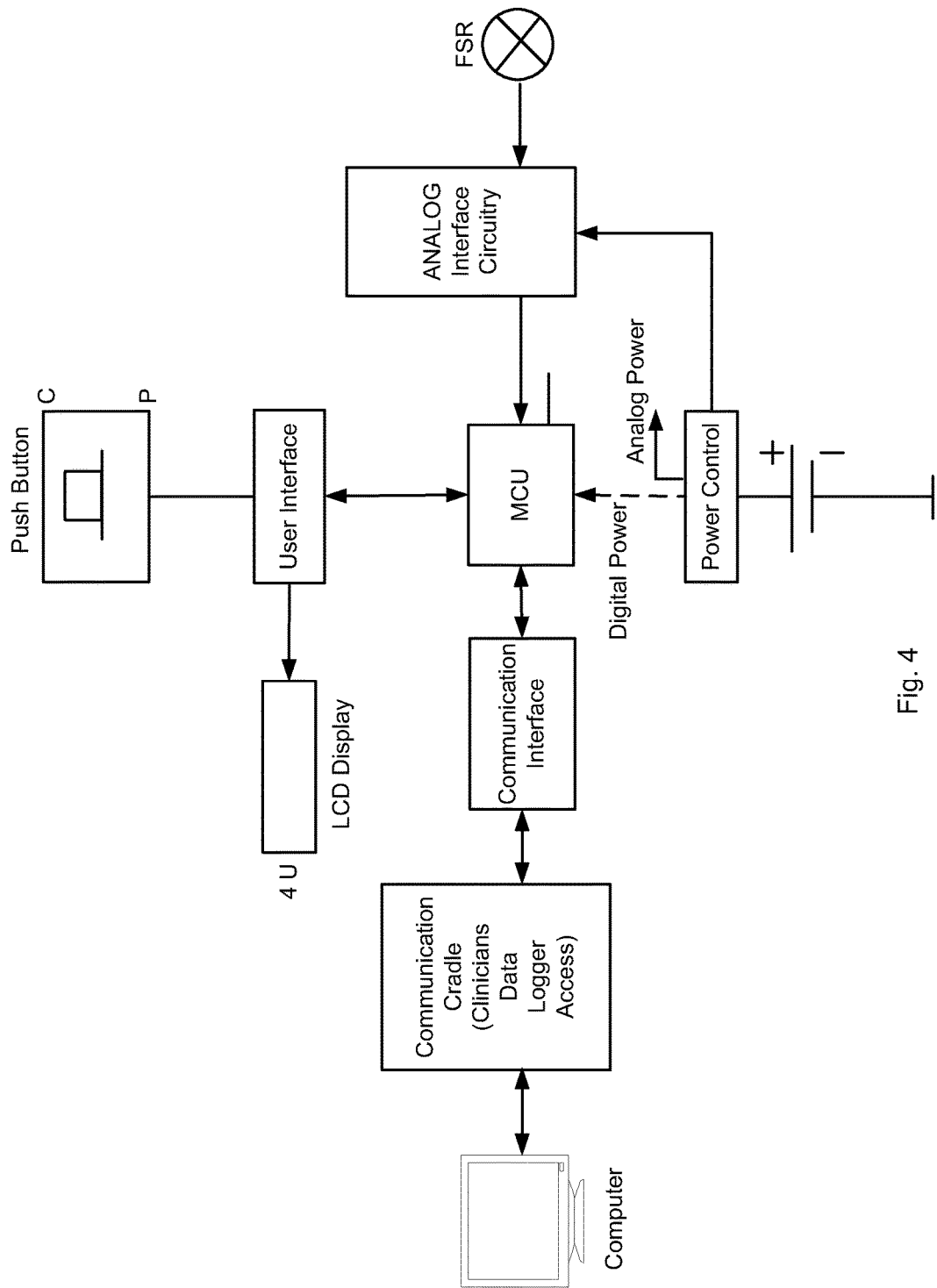
FIG. 4 shows a block diagram of the dose counter.

FIG. 4 is a block diagram showing the functionality of the dose counter. A microcontroller unit (MCU) interfaces with the analog circuitry and force sensor, and enables communications with an external cradle for data transfer via a communication interface. Note that by further comprising a time-measurement component, such as watch-type quartz oscillator shown in FIG. 2B, the time-measurement can be stabilized. Furthermore, the provision of sufficient memory within the dose counter device enables the history of the doses taken over time to be recorded. This history recording enables subsequent downloading of this history by medical personnel. The downloading may be performed via either a physical connection means such as the connector 19 shown in FIG. 1 or via a contactless interface means such as induction or wireless, to an external computer (such as the medical practitioner's PC), for display and/or analysis and/or storage.

The addition of an electronic dose counter (whether such as that provided above or otherwise implemented) enables the implementation of a method of recording and downloading the history of the doses taken, and associating this history with a specific day and time. Possible methods for associating the dosing history with a specific date and time include the following:

1) In one embodiment, the dose counter has its internal clock set at time of manufacture, assembly or distribution, so that the actual time and date of taking each dose can be recorded. As the dose counter may be used in different countries, it is simplest to set the date and time at manufacture or assembly according to a standard such as GMT. By providing a function in the medical practitioner's software to define the offset between the local date-time and GMT, the local date and time of each dose may be displayed on the medical practitioner's computer.

2) Alternatively, the dose counter stores relative time and/or time intervals between doses rather than absolute time. Advantageously, this obviates the need to have the internal clock set to a specific time. According to one embodiment of this method, the first dose marks the starting point ($T_1=0$) of recording a relative-time index, where the dose counter accumulates the time in minutes thereafter. The next dose may take place after 4 hours and would therefore be time-stamped as occurring at $T_2=240$, etc. When the dose counter is interfaced to the medical practitioner's computer, the actual time as either stored on that computer (or downloaded from a central time server such as NTP) is then used to assign the actual times to the dose timestamps. For example if at that point the internal timer in the above example shows 480 minutes since the starting point and the current time is 4 pm, then the first dose took place 480 minutes (i.e. 8 hours) ago, and therefore that dose can be shown as having taken place at 8 am that same day, with the second dose having been taken at 12 noon. This mapping of the relative times stored in the dose counter's memory, to actual local time can take place each time that dosage information is downloaded. Alternatively, the down-loading process can involve resetting the relative time setting in the dose counter to an absolute time, so that the dose counter then goes over to a mode of time-stamping the doses in terms of the actual time.

Although the above examples describe the communication as taking place though a wired connection to the medical practitioner's computer, these are just examples and the scope of the method should be understood to encompass any type of communication between a dose counter and an external computer, whether wired or wireless, and any kind of remote displaying or analyzing device whether a handheld computer or a central health-system one. Thus the dose counter history could be uploaded wirelessly from a Bluetooth™/WiFi-enabled cradle to a remote computer via the cellular network. Likewise the display and or analysis device can be a hand-held computer or smart phone, which can optionally serve to store the dosing history.

The dose recording and downloading method of the present invention also provides the functionality to make use of time-stamped dose history uploaded by an electronic dose counter to an external host system, such as a doctor's computer, for more extensive analysis. Such functionality can include integrating the uploaded history over time, whereby data from both the current inhaler device and previous ones are displayed in tabulated or graphical form along a common time axis. Advantageously, as some patients have two or more different types of inhaler, this functionality enables data relating to the presentation and/or analysis of the history of use of multiple inhalers (of all types) used by the patient to be superimposed. This can give a clear picture of the patient's medical history, for example how often he has used a rescue inhaler and at what times of the day.

As is standard on MDIs and many other drug products, the prescribing information provides dosing information and/or other instructions. In the specific case of an MDI with a dose counter which stores the dosing history (as per the current invention), this prescribing information can additionally perform the role of conveying a recommendation to the medical practitioner. Such recommendation may be not to change a medication regimen until the patient's dosing history has been evaluated for compliance with the intended regimen. For example, the medical practitioner may believe that, as the patient is apparently not responding to (or properly "controlled" by) the medication, the patient should be given a more potent drug. However, the purpose of the recommendation on the prescribing information is to ensure that the medical practitioner does not make this determination without first reviewing the patient's actual compliance history. If, on review of the dosing history, it transpires that the patient has not been taking the drug as required, then the medical practitioner should take this fact into account. This method of treating a patient increases the likelihood that a patient will not be prescribed a new medication regimen unless a previous regimen—with which he was verified to be compliant—is shown to be ineffective.

Figure 5:
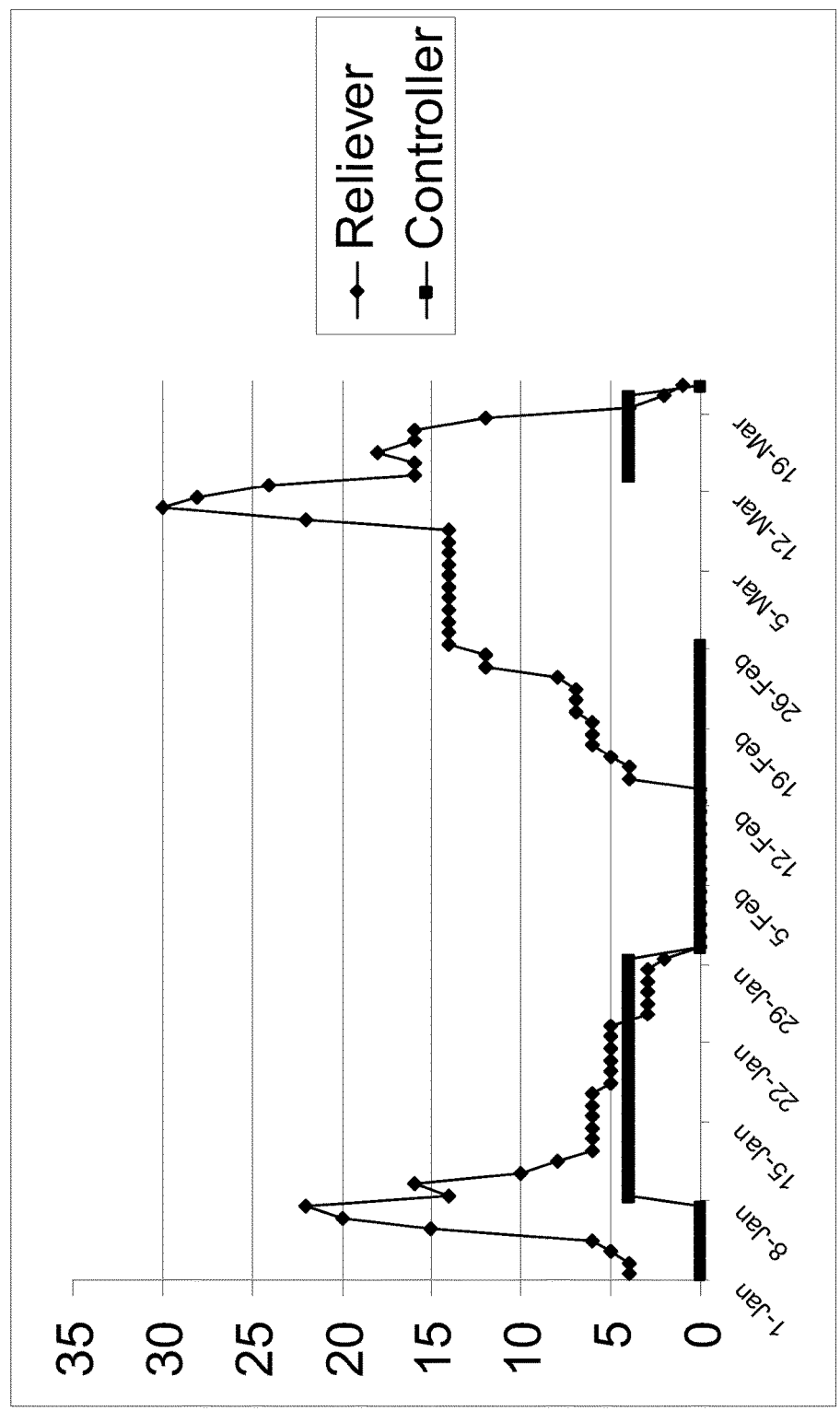
FIG. 5 provides an example of a medical practitioner's screen-shot showing the integrated dosage history from two MDI devices, each for delivering a different drug.

Typical MDI drugs for asthma include both controller and reliever medications. Controllers such as an inhaled corticosteroid serve to reduce the likelihood of having an asthma attack. Reliever drugs, such as Beta2-antagonists, on the other hand, serve to respond to an asthma attack when it occurs. The use of a dose counter having download capability on both types of inhaler enables the medical practitioner to show the dosage history from both MDIs in a unified picture as illustrated in FIG. 5. This provides the medical practitioner with a clear picture of whether the patient is "controlled" with his existing medication, or uncontrolled; and also whether the lack of control was due to the patient failing to take his medication as prescribed. In this way, a method of treatment can be implemented whereby the prescribing information for the MDI recommends to the medical practitioner to check the dosage history of the patient—across one or more drug types—before making any changes to the patient's medication.

In one embodiment, the dose history may be stored as an Internet-based application. In this embodiment, the dosing history is stored on a web server and the patient and the medical practitioner can view this history through their computers, preferably by viewing the appropriate web application through a browser.

In order to minimize the power consumption of the dose controller, a push button as shown in the block diagram may be activated by the initial force applied to the upper surface 20 of the dose counter, such that that the circuit is then activated and the change of force applied over time monitored by the microcontroller unit (MCU) thus awakened. To this end it is preferable to use a microcontroller which can be re-activated very quickly, such as the MSP430F4132IPM microcontroller from Texas Instruments. Advantageously, this enables the limited power supply supplied by a small battery to maintain both the timekeeping function and the time-stamping of the dose recording to work over a long time period extending as far as a few years. This is desirable as the inhalers may have a long shelf-life, followed by a year or two of occasional use.

In conclusion, the invention provides a dose counter based on integrating an electronic module into the base of an MDI canister, the dose counter being capable of measuring the number of doses delivered and displaying the number of doses delivered or remaining via an electronic display means. The dose counter uses a force sensor to detect the action of depressing the canister into the MDI housing in order to deliver the dose, and thus does not depend on the measurement of physical travel. Also described is a method for recording and downloading the dosing history. Although some preferred embodiments have been described, the invention is not limited to the specific embodiments as described and is limited only the scope of the appended claims.

What is claimed:

1. A dose counter for an inhaler, the dose counter comprising:
   a base configured to attach the dose counter to a medication canister;
   a sensor configured to sense a force applied to the dose counter; and
   an electronic controller configured to measure a time duration of the force,
   wherein said electronic controller is further configured to count a dose as being delivered from the medication canister if the measured time duration exceeds a first threshold.

2. The dose counter of claim 1, wherein the sensor is further configured to measure the force, and
   wherein the electronic controller is further configured to count the dose as being delivered if the measured force exceeds a second threshold.

3. The dose counter of claim 2, wherein the first threshold comprises a minimum time duration and the second threshold comprises a minimum force.

4. The dose counter of claim 1, wherein the sensor comprises one of a force sensor, a force sensitive resistor, a pressure sensor, a pressure sensitive resistor, a piezoelectric sensor, a strain gauge, or a MEMS-based sensing device.

5. The dose counter of claim 1, further comprising a display configured to indicate a number of remaining doses.

6. The dose counter of claim 1, further comprising a display configured to indicate that the dose is due to be taken.

7. The dose counter of claim 1, wherein the dose counter is further configured to wirelessly upload dosing history data to a remote wireless device.

8. A method for counting doses delivered from an inhaler, the method comprising:
   sensing a force applied to a dose counter attached to a medication canister;
   measuring a time duration of the force; and
   counting a dose as being delivered from the medication canister if the measured time duration exceeds a first threshold.

9. The method of claim 8, further comprising measuring the force and counting the dose as being delivered if the measured force exceeds a second threshold.

10. The method of claim 9, wherein the first threshold comprises a minimum time duration and the second threshold comprises a minimum force.

11. The method of claim 8, wherein the sensing is performed by one of a force sensor, a force sensitive resistor, a pressure sensor, a pressure sensitive resistor, a piezoelectric sensor, a strain gauge, or a MEMS-based sensing device.

12. The method of claim 8, further comprising displaying a number of remaining doses.

13. The method of claim 8, further comprising displaying at least one icon indicating that the dose is due to be taken.

14. The method of claim 8, further comprising wirelessly uploading dosing history data to a remote wireless device.

15. An inhaler comprising:
    a housing configured to receive a medication canister;
    a sensor configured to sense a force applied to the medication canister; and
    an electronic controller configured to measure a time duration of the force,
    wherein said electronic controller is further configured to count a dose as being delivered from the medication canister if the measured time duration exceeds a first threshold.

16. The inhaler of claim 15, wherein the sensor is further configured to measure the force, and
    wherein the electronic controller is further configured to count the dose as being delivered if the measured force exceeds a second threshold.

17. The inhaler of claim 16, wherein the first threshold comprises a minimum time duration and the second threshold comprises a minimum force.

18. The inhaler of claim 15, wherein the sensor comprises one of a force sensor, a force sensitive resistor, a pressure sensor, a pressure sensitive resistor, a piezoelectric sensor, a strain gauge, or a MEMS-based sensing device.

19. The inhaler of claim 15, further comprising a display for indicating a number of remaining doses.

20. The inhaler of claim 15, further comprising a display for indicating that the dose is due to be taken.

21. The inhaler of claim 15, wherein the inhaler is further configured to wirelessly upload dosing history data to a remote wireless device.

* * * * *